(12) United States Patent
Dupuis et al.

(10) Patent No.: US 9,795,565 B2
(45) Date of Patent: Oct. 24, 2017

(54) METHOD FOR PREPARING A VACCINE COMPOSITION COMPRISING AT LEAST ONE ANTIGEN AND AT LEAST ONE ADJUVANT

(75) Inventors: Laurent Dupuis, Reims (FR); Jérôme Gaucheron, Castres (FR); Olivier Braun, Castres (FR)

(73) Assignee: Société d'Exploitation de Produits pour les Industries Chimiques SEPPIC, Paris (FR)

( * ) Notice: Subject to any disclaimer, the term of this patent is extended or adjusted under 35 U.S.C. 154(b) by 1708 days.

(21) Appl. No.: 12/739,389

(22) PCT Filed: Oct. 6, 2008

(86) PCT No.: PCT/FR2008/051807
§ 371 (c)(1),
(2), (4) Date: Apr. 22, 2010

(87) PCT Pub. No.: WO2009/053601
PCT Pub. Date: Apr. 30, 2009

(65) Prior Publication Data
US 2010/0233196 A1 Sep. 16, 2010

(30) Foreign Application Priority Data
Oct. 24, 2007 (FR) ...................................... 07 58542

(51) Int. Cl.
| A61K 47/32 | (2006.01) |
| A61K 9/127 | (2006.01) |
| A61K 9/00 | (2006.01) |
| A61K 47/44 | (2017.01) |

(52) U.S. Cl.
CPC ............ *A61K 9/127* (2013.01); *A61K 9/0019* (2013.01); *A61K 47/32* (2013.01); *A61K 47/44* (2013.01)

(58) Field of Classification Search
None
See application file for complete search history.

(56) References Cited

U.S. PATENT DOCUMENTS

| 2,798,053 A | 7/1957 | Brown |
| 5,373,044 A | 12/1994 | Adams et al. |
| 5,422,109 A | 6/1995 | Brancq et al. |
| 5,801,157 A | 9/1998 | Ganne |
| 2001/0028884 A1 | 10/2001 | Poulet |
| 2004/0170640 A1* | 9/2004 | Gerber ....................... 424/184.1 |
| 2005/0002977 A1 | 1/2005 | Mallo |
| 2005/0048016 A1* | 3/2005 | Lebreton et al. .......... 424/70.12 |

FOREIGN PATENT DOCUMENTS

| EP | 0 301 532 A2 | 1/1989 |
| EP | 0 301 532 A3 | 1/1989 |
| EP | 1 496 081 A1 | 1/2005 |
| WO | WO 91 00107 A1 | 1/1991 |
| WO | WO 94 16681 A1 | 8/1994 |
| WO | WO 95 25542 A1 | 9/1995 |
| WO | WO 98 17310 A2 | 4/1998 |
| WO | WO 98 17310 A3 | 4/1998 |
| WO | WO 99 20305 A1 | 4/1999 |
| WO | WO 99 20305 A8 | 4/1999 |
| WO | WO 03 024354 A2 | 3/2003 |
| WO | WO 03 024354 A3 | 3/2003 |

OTHER PUBLICATIONS

PCT Written Opinion for PCT/FR2008/051807, 2008.
International Search Report for PCT/FR2008/051807, 2008.
Ash, M. et al. "Thesaurus of Chemical Products," Chemical Publishing Co., Inc., vol. I, 1986, p. 211.
Cox, G.J.M. et al., "Bovine herpesvirus 1: Immune responses in mice and cattle injected with plasmid DNA", Journal of Virology, vol. 67, No. 9, Sep. 1993, pp. 5664-5667.
Eliot, M. et al., "Construction of a defective adenovirus vector expressing the pseudorabies virus glycoprotein gp50 and its use as live vaccine", Journal of General Virology (1990), 71, pp. 2425-2431.
Lin, H. et al., "Expression of recombinant genes in myocardium in vivo after direct injection of DNA", Circulation, vol. 82, No. 6, Dec. 1990, pp. 2217-2221.

* cited by examiner

*Primary Examiner* — Yunsoo Kim
(74) *Attorney, Agent, or Firm* — Allen E. White

(57) ABSTRACT

Method for preparing a vaccine, comprising—a step a) of preparing an adjuvant composition by dispersing, in a physiologically acceptable aqueous solution, at least one inverse latex or a powder of polymer resulting from the atomization of said inverse latex; —a step b) of mixing the composition obtained in step a) into an antigenic medium, intended to form a vaccine composition.

11 Claims, 2 Drawing Sheets

Figure 1:
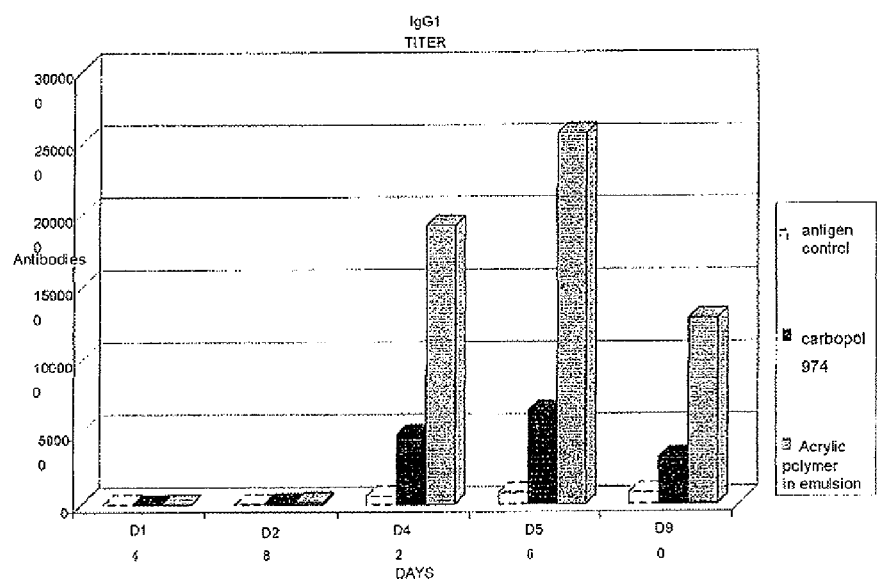

Immunological results/comparison microgel obtained in emulsion with polyacrylate obtained in solvent phase (carbopol® 974)

Innocuousness results/comparison microgel obtained in emulsion with polyacrylate obtained in solvent phase (carbopol® 974)/local reaction positive control: W/O emulsion

METHOD FOR PREPARING A VACCINE COMPOSITION COMPRISING AT LEAST ONE ANTIGEN AND AT LEAST ONE ADJUVANT

This application is a 371 of International PCT Application PCT/FR2008/051807, filed Oct. 6, 2008, the entire contents of which are incorporated herein by reference.

FIELD OF THE INVENTION

The present invention relates to a method for preparing a vaccine composition comprising at least one antigen, in particular an antigen of viral, bacterial or parasitic origin, and at least one adjuvant.

BACKGROUND

The development of inactivated vaccines or vaccines containing purified antigens is increasingly important since it makes it possible to avoid adverse side effects in the individual treated. However, the improvement in the quality of antigens occurs to the detriment of the immunogenic nature of said antigens. This is why they are combined with adjuvants of immunity.

Adjuvants of immunity are products which increase immune system reactions, when they are administered in the presence of antigens of viral, bacterial or synthetic origin. They bring about the massive appearance of macrophages at the injection site, and then in the lymph nodes, increase the production of specific immunoglobulins, the antibodies, and stimulate numerous cells involved in immune defense mechanisms.

These adjuvants are of diverse natures. They may, for example, consist of emulsions which are in the form of water-in-oil W/O, or oil-in-water O/W, or water-in-oil-in-water W/O/W, or oil-in-water-in-oil O/W/O emulsions.

Freund's adjuvants are very effective; they result from the combination of a mineral oil and of a mannitol ester optionally containing a killed mycobacterium. Vaccines prepared by mixing, in equal parts, a Freund's adjuvant with an aqueous antigenic medium still remain the references throughout the world for laboratory studies. They are in the form of water-in-oil W/O emulsions, i.e. of emulsions for which the continuous phase is constituted of an oil or a mixture of oils, and the dispersed phase is an aqueous phase that may comprise solubilizing excipients such as, for example, glycerol or dimethyl sulfoxide. The active ingredient is generally located in the aqueous phase, which is commonly a buffered saline solution. This phase is in the form of drops separated from one another by an oily film. This formulation makes it possible to obtain amplified biological responses sustained over time.

However, emulsions of this W/O type are generally very viscous and are therefore difficult to inject. They often require the use of syringes with a large needle diameter and cause pain during the injection and trauma at the injection site.

The aqueous phase content by mass of injectable W/O emulsions is around 30% to 40% for 100% of the mass of the emulsion. The maximum content by mass encountered is 30%. However, this limit constitutes an impairment in particular to the development of polyvalent vaccines, in which several antigens are combined and for which it would be preferable to obtain W/O emulsions having aqueous phase contents of greater than 50% by mass.

However, in a W/O emulsion with a low aqueous phase content, up to approximately 20% by mass, the viscosity of the emulsion is very close to the viscosity of the oil. Increasing the proportion by mass of aqueous phase increases its viscosity. Thus, an emulsion containing 20% by mass of water, having a viscosity of 100 mPa·s, measured using a Brookfield LVT viscometer fitted with a No. 2 spindle revolving at a speed of 60 revolutions per minute, changes into a cream that is very difficult to inject when the water content is increased up to 50% by mass.

Some commercial oily adjuvants which are in the form of W/O emulsions, such as Montanide™ ISA 70, make it possible to obtain injectable W/O emulsions containing approximately 30% by weight of aqueous phase and 70% by weight of oily phase and having viscosities of the order of 50 to 100 mPa·s measured using a Brookfield LVT viscometer fitted with a No. 2 spindle revolving at a speed of 60 revolutions per minute. Other adjuvants, such as Montanide™ ISA 50V2, make it possible to obtain injectable W/O emulsions containing approximately 50% by weight of aqueous phase and 50% by weight of oily phase and having viscosities of less than 250 mPa·s, measured using a Brookfield LVT viscometer fitted with a No. 2 spindle revolving at a speed of 60 revolutions per minute.

The international patent application published under the number WO 99/20305 discloses the use of mannitol oleate-based surfactants with mineral oils such as Marcol™ 52 for preparing "fluid" emulsions having viscosities of the order of 500 mPa·s measured using a Brookfield LVT viscometer fitted with a No. 2 spindle revolving at a speed of 60 revolutions per minute.

The notion of a fluid emulsion depends largely on the field of application. For injectable emulsions, the upper viscosity limit for a fluid emulsion is defined with respect to the viscosity of a reference W/O emulsion which contains 50% by mass of aqueous phase and 50% by mass of incomplete Freund's adjuvant (IFA); this viscosity, measured using a Brookfield LVT viscometer fitted with a No. 3 spindle revolving at a speed of 30 revolutions per minute, is of the order of approximately 2000 mPa·s. This emulsion is considered to be very viscous.

A W/O emulsion will be said to be fluid if its viscosity is less than a quarter of that of this reference emulsion, i.e. less than 500 mPa·s at 25° C., measured using a Brookfield LVT viscometer fitted with a No. 2 spindle and revolving at a speed of 30 revolutions per minute.

However, fluid emulsions are generally less stable than more viscous emulsions, since phase separations at ambient temperature are observed only a few days after preparation of said emulsions.

Aqueous phase thickening polymers in the form of powders exist, such as acrylic acid homopolymers in the sodium forms thereof or copolymers based on acrylic acid and its esters. Mention will, for example, be made of the polymers sold by the company Noveon under the trade mark Carbopol™ and Pemulen™. They are described in particular in U.S. Pat. No. 5,373,044 and U.S. Pat. No. 2,798,053 and in European patent EP 0 301 532. These polymers were initially developed as thickeners for thickening formulations essentially intended for cosmetic applications, and which have been described and used for many years. These polymers are obtained from a monomer such as, for example, acrylic acid, methacrylic acid, acrylic acid esters or methacrylic acid esters in solution in an organic solvent phase.

During the polymerization reaction, obtained by adding various catalysts under specific temperature and pressure conditions, the polymer becomes insoluble in the initial solvent phase and precipitates at the bottom of the reactor. This process is called "precipitation polymerization".

The polymers thus obtained, the most well-known grades of which are the Carbopols©, are very effective thickeners that are very widely used in the cosmetics industry. These polymers are also used for varied pharmaceutical applications:

- preparation of delayed-release-effect polymer matrices,
- preparation of polymer gels, and complexation of said polymers with proteins,
- preparation of polymer films creating protection during contacting with biological fluids,
- preparation of bioadhesive formulations providing greater persistence during application to the mucous membranes,
- preparation of vaccine adjuvants.

The use as a vaccine adjuvant, with final polymer contents by mass of the order of "one percent", is in the form of a readily injectable, translucent, fluid vaccine.

The adjuvant properties of synthetic substances are very closely linked to their physical forms at the time of administration. Thus, the size of particles used to trigger a large adjuvant effect is a major parameter which will control the possibility of picking up by the immunocompetent cells. Furthermore, depending on the size of the particles, it will also be possible to orient the response toward antibody production (humoral response) or rather for stimulating specific immune system cells (cellular response). The synthesis of microspheres of various polymers in a solvent phase in the form of dispersions is widely described in the literature with the possibility of encapsulation of a biologically active agent (which may be an antigen in the case of vaccines) or being used as an adsorption support for carrying and presenting an active agent bound to the external surface of the microspheres by more or less strong interactions.

The controlling of the size of the adjuvant particles is a constant challenge since it must be accompanied by stability of these adjuvant particles over time. It is important in particular to avoid aggregations during storage or phase separations. The controlling of the size must also be accompanied by stability of the composition, after injection into the living being, in particular owing to stresses linked to variation in pH, to the presence of enzymes, to temperature variations.

SUMMARY OF THE INVENTION

The present invention relates to a method for preparing a vaccine that comprises a step a) of preparing an adjuvant composition by dispersing, in a physiologically acceptable aqueous solution, at least one inverse latex or a powder of polymer resulting from the atomization of said inverse latex. This step is followed by a step b) of mixing the composition obtained in step a) into an antigenic medium, intended to form a vaccine composition. The present invention further relates to the use of the adjuvant composition of step a) for the preparation of a vaccine composition and for the use of at least one inverse latex or of a powder of polymer resulting from the atomization of the inverse latex for preparing a vaccine.

BRIEF DESCRIPTION OF THE FIGURES

FIG. 1 illustrates immunological results/comparison microgel obtained in the emulsion with polyacrylate obtained in solvent phase (Carbopol® 974).

FIG. 2 illustrates innocuous results/comparison microgel obtained in emulsion with polyacrylate obtained in solvent phase (Carbopol® 974)/local reaction positive control: W/O emulsion.

DETAILED DESCRIPTION OF THE INVENTION

The applicant has sought to develop an original technology for the synthesis of polymers for controlling the size of the aggregates of polymers (or "microgels") thus providing very good adjuvant effectiveness. For this, the water-in-oil W/O emulsion, or inverse emulsion, polymerization technology is used to prepare these polymers. Specifically, the size of the drops of monomer solution is controlled by using emulsifying surfactant systems of water-in-oil type suitable for W/O emulsion technologies. In general, it involves coupling a lipophilic emulsifying surfactant, having for example an HLB of between 2 and 7, with a hydrophilic emulsifying surfactant, having for example an HLB of between 10 and 15, with a weighted average value which provides a homogeneous W/O emulsion. The monomers are polymerized by adding catalysts and other crosslinking agents at the usual concentrations under pH and temperature conditions suitable for a complete reaction of the monomer so as to form polymers.

The size of the adjuvant particles has a direct impact on the immunological properties of the formulations containing them. In addition, depending on the species having to be vaccinated and on the type of vaccine under consideration, the optimal size of the particles may differ. By means of know-how in the formulation of emulsions (optimization of the HLB, nature of the surfactants, concentration, process), it is possible, during the inverse-emulsion synthesis process, to control the distribution of the drop size of the emulsion and thus the average size and the particle size distribution of the aggregates. The term "dispersion" is intended to mean, according to the surfactant content and the shear energy provided during the emulsification step, heterogeneous systems that may be:

- suspensions,
- emulsions,
- microemulsions.

These various dispersed forms make it possible to control the size dispersion of the microgels in ranges of from 50 nm to 100 μm.

The chemical conditions for synthesis of the polymer (types of monomers, catalysts, initiators) make it possible to control the individual properties of the polymer obtained (average molar mass, crosslinking, anionic nature).

The adjuvant thus synthesized is in the form of a "drops of polymer in oil" or "inverse latex" emulsion. When this emulsion is dispersed in an aqueous solution of antigen containing a physiological buffer, it inverts and disperses so as to give a translucent fluid dispersion of polymer microgels in water. For example, drops of poly(sodium acrylate) microgels can have an average size of between 0.5 and 5 micrometers, for example approximately 2 micrometers.

The subject of the invention is a method for preparing a vaccine using an inverse latex. More particularly, the subject of the invention is a method for preparing a vaccine, comprising:

- a step a) of preparing an adjuvant composition by dispersing, in a physiologically acceptable aqueous solution, at least one inverse latex or a powder of polymer resulting from the atomization of said inverse latex;

a step b) of mixing the composition obtained in step a) into an antigenic medium, intended to form a vaccine composition.

The term "inverse latex" is intended to mean a water-in-oil emulsion of polymer, in which the aqueous phase, dispersed in the continuous oily phase, contains said polymer. The inverse latex, resulting from the inverse emulsion polymerization, is therefore in the form of a liquid emulsion. Subsequent atomization of this inverse latex may, if necessary or if desired, be carried out so as to form said powder of polymer. The atomization is, for example, described in European patent application EP 1 496 081.

The term "physiologically acceptable aqueous solution" denotes, in the context of the present invention, aqueous solutions which are able to be used in the preparation of vaccines, whether this involves, for example, water of quality in accordance with the pharmacopeias, in particular European or US pharmacopeias, for instance physiological salines, or saline and/or, where appropriate, aqueous-alcoholic solutions in accordance with said pharmacopeias.

The term "adjuvant composition" denotes a composition which is an adjuvant of immunity.

At least one surfactant of hydrophilic nature may also be added, prior to this step a), so as to improve the stability of such a dispersion over time.

The term "surfactant of hydrophilic nature" denotes emulsifying surfactants having an HLB value which is sufficiently high, between 10 and 15, to give stable oil-in-water emulsions, such as ethoxylated mannitan esters or ethoxylated sorbitan esters, for instance the sorbitan oleate ethoxylated with 20 mol of ethylene oxide, sold by the company SEPPIC under the name Montanox™ 80.

The term "antigenic medium" denotes a medium comprising at least one antigen or at least one in vivo generator of a compound comprising an amino acid sequence. The expression "antigen or at least one in vivo generator of a compound comprising an amino acid sequence" denotes either killed microorganisms, such as viruses, bacteria or parasites, or purified fractions of these microorganisms, or live microorganisms of which the pathogenic capacity has been attenuated. By way of examples of viruses that can constitute an antigen according to the present invention, there is the rabies virus, herpesviruses, such as the Aujeszky's disease virus, orthomixoviruses such as influenzae, picornaviruses such as the foot-and-mouth disease virus, or retroviruses such as HIVs. By way of microorganisms of the bacterial type that can constitute an antigen according to the present invention, mention may be made of *E. coli*, and microorganisms of the *Pasteurella, Furunculosis, Vibriosis, Staphylococcus* and *Streptococcus* genera. By way of examples of parasites, mention may be made of those of the *Trypanosoma, Plasmodium* and *Leishmania* genera. Mention may also be made of recombinant viruses, in particular nonenveloped viruses, such as adenoviruses, the vaccinia virus, the canarypox virus, herpesviruses or baculoviruses. Also denoted is a live, nonenveloped, recombinant viral vector, the genome of which contains, preferably inserted into a part that is not essential for replication of the corresponding enveloped virus, a sequence encoding an antigenic subunit which induces antibody synthesis and/or a protective effect against the abovementioned enveloped virus or pathogenic microorganism; these antigenic subunits may, for example, be a protein, a glycoprotein, a peptide or a fraction which is a peptide fraction and/or protective against an infection with a living microorganism such as an enveloped virus, a bacterium or a parasite. The exogenous gene inserted into the microorganism may, for example, be derived from an Aujeszky's disease virus or an HIV virus.

Mention may in particular be made of a recombinant plasmid made up of a nucleotide sequence, into which an exogenous nucleotide sequence, originating from a pathogenic microorganism or virus, is inserted. The aim of the latter nucleotide sequence is to allow the expression of a compound comprising an amino acid sequence, the aim of this compound itself being to trigger an immune reaction in a host organism.

The expression "in vivo" generator of a compound comprising an amino acid sequence is intended to mean an entire biological product capable of expressing said compound in the host organism into which said in vivo generator has been introduced. The compound comprising the amino acid sequence may be a protein, a peptide or a glycoprotein. These in vivo generators are generally obtained by methods derived from genetic engineering. More particularly, they may consist of living microorganisms, generally a virus, playing the role of a recombinant vector, into which is inserted a nucleotide sequence, in particular an exogenous gene. These compounds are known in themselves, and are used in particular as recombinant subunit vaccines. In this respect, reference may be made to the article by M. Eloit et al., Journal of virology (1990) 71, 2925-2431 and to the international patent applications published under the numbers WO-A-91/00107 and WO-A-94/16681. The in vivo generators according to the invention can also consist of a recombinant plasmid which comprises an exogenous nucleotide sequence, and which is capable of expressing, in a host organism, a compound comprising an amino acid sequence. Such recombinant plasmids and their method of administration to a host organism were described in 1990 by Lin et al., Circulation 82:2217, 2221; Cox et al., J. of Virol, September 1993, 67, 9, 5664-5667 and in the international application published under the number WO 95/25592. Depending on the nature of the nucleotide sequence included in the in vivo generator, the compound comprising the amino acid sequence which is expressed within the host organism can:

(i) be an antigen, and enable the triggering of an immune reaction,
(ii) have a curative action with respect to a disease, essentially a disease of a functional nature, which has been triggered in the host organism. In this case, the in vivo generator enables gene therapy type treatment of the host.

By way of example, such a curative action can consist of synthesis, by the in vivo generator, of cytokines, such as interleukins, in particular interleukin-2. These interleukins allow the triggering or the reinforcement of an immune reaction directed toward selective elimination of cancer cells.

The vaccine composition as defined above comprises an antigen concentration which depends on the nature of this antigen and on the nature of the individual treated. It is, however, particularly noteworthy that an adjuvant according to the invention makes it possible to significantly decrease the usual antigen dose required. The suitable antigen concentration can be determined conventionally by those skilled in the art. Generally, this dose is about $0.1\ \mu g/cm^3$ to $1\ g/cm^3$, more generally between $1\ \mu g/cm^3$ and $100\ mg/cm^3$. The concentration of said in vivo generator in the composition according to the invention depends, here again, in particular on the nature of said generator and on the host to which it is administered. This concentration can be readily determined by those skilled in the art, on the basis of routine experiment. By way of indication, when the in vivo generator is a recombinant microorganism, its concentration in the composition according to the invention is in general between $10^2$ and $10^{15}$ microorganisms/cm$^3$, and preferably between $10^5$ and $10^{12}$ microorganisms/cm$^3$. When the in vivo generator is a recombinant plasmid, its concentration in the composition obtained according to the method which is the subject of the invention can be between 0.01 g/dm$^3$ and 100 g/dm$^3$. The vaccine, as defined above, is prepared by mixing the adjuvant phase and the antigenic phase, optionally adding water or a pharmaceutically acceptable diluent medium.

The oily continuous phase, used for preparing the inverse latex used during step a) of the method which is the subject of the present invention, comprises one or more compounds chosen from oils of mineral, plant or animal origin, alkyl esters of said oils, alkyl esters of fatty acids or alkyl ethers of fatty acids, fatty acid esters of polyols or fatty alcohol ethers of polyols, and synthetic oils.

A commercial mineral oil may also be used, i.e. a commercial mineral oil containing saturated hydrocarbons, such as paraffins, isoparaffins or cycloparaffins, having, at ambient temperature, a density of between 0.7 and 0.9 and a boiling point above 180° C., such as, for example, Exxsol™ D 100 S or Marcol™ 52, sold by the company Exxon Chemical, isohexadecane or isododecane, or a mixture of several of these oils.

According to one preferred aspect of the present invention, the oil phase is made up of Marcol™ 52 or of isohexadecane; isohexadecane, which is identified in Chemical Abstracts by the RN number=93685-80-4, is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9). It is sold in France by the company Bayer. Marcol™ 52 is a commercial oil corresponding to the French Codex definition of liquid petroleum jellies. It is a white mineral oil in accordance with FDA regulations CFR 172.878 and CFR 178.3620 (a) and is listed in the US pharmacopeia US XXIII (1995) and in the European pharmacopeia (1993).

As examples of oils of plant origin, mention is made of groundnut, olive, sesame, soya bean, wheatgerm, grapeseed, sunflower, castor, flax, corn, copra, palm, walnut, hazelnut or rapeseed oils, or else squalene or squalane of plant origin sold in France by the company Sophim, under the name Phytosqualan™, identified in Chemical Abstracts by the RN number=111-01-3, and which consists of a mixture of hydrocarbons containing more than 80% by weight of 2,6,10,15,19,23-hexamethyl-tetracosane.

As examples of oils of animal origin, mention is made of spermaceti oil, tallow oil, squalane or squalene extracted from fish livers.

As examples of alkyl esters of oils, mention is made of methyl, ethyl, linear or branched propyl or linear or branched butyl esters of said oils.

As fatty acids suitable for the preparation of the esters mentioned above, mention is more particularly made of those containing from 12 to 22 carbon atoms, such as, for example, myristic acid, paimitic acid, oleic acid, ricinoleic acid or isostearic acid, and advantageously a fatty acid that is liquid at 20° C.

As examples of fatty acid esters or of fatty acid ethers, mention is made of alkyl esters of fatty acids, such as ethyl oleate, methyl oleate, isopropyl myristate or octyl palmitate, fatty acid esters of polyols or fatty alcohol ethers of polyols, such as fatty acid monoglycerides, fatty acid diglycerides, fatty acid triglycerides, esters of fatty acids with a polyglycerol or fatty acid esters of propylene glycol, and more particularly esters of fatty acids with a hexyl, for instance sorbitol or mannitol, and esters of fatty acids with a hexyl anhydride, such as sorbitan or mannitan.

As examples of synthetic oils, mention is made of hydrogenated polydecene or hydrogenated polyisobutene, sold in France by the company Ets B. Rossow and Cie under the name Parleam—Polysynlane™, which is cited by Michel and Irene Ash, "Thesaurus of Chemical Products", Chemical Publishing Co, Inc. 1986 Volume I, page 211 (ISBN 0 7131 3603 0).

In the context of the present invention, the oily continuous phase, used to prepare the inverse latex used during step a) of the method which is the subject of the present invention, can comprise just one of the compounds mentioned above or else a mixture of several of the compounds mentioned above.

The proportion of the oily phase in the inverse latex is between 10% and 50% by mass, and preferably between 15% and 25% by mass, of the total mass of the inverse latex.

Said at least one polymer obtained by inverse emulsion polymerization resulting in the inverse latex forming the basis of the preparation of the adjuvant composition prepared during step a) of the method which is the subject of the invention, is chosen from branched or crosslinked anionic polyelectrolytes chosen from acrylic acid/2-methyl-[(1-oxo-2-propenyl)amino]-1-propanesulfonic acid (AMPS) copolymers, acrylamide/2-methyl-[(1-oxo-2-propenyl)amino]-1-propanesulfonic acid copolymers, 2-methyl-[(1-oxo-2-propenyl)amino]-1-propanesulfonic acid/(2-hydroxyethyl) acrylate copolymers, partially or totally salified 2-methyl-[(1-oxo-2-propenyl)amino]-1-propanesulfonic acid homopolymer, partially or totally salified acrylic acid homopolymer, partially or totally salified methacrylic acid homopolymer, acryloyl ethyl trimethyl ammonium chloride/acrylamide copolymers, AMPS/vinylpyrrolidone copolymers, AMPS/N-methylacrylamide copolymers, AMPS/N,N-dimethylacrylamide copolymers, AMPS/meth-acrylamide copolymers, AMPS/N-isopropylacrylamide copolymers, AMPS/N-[2-hydroxy-1,1-bis(hydroxy-methyl)ethyl]propenamide [or tris(hydroxy-methyl)acrylamidomethane or N-tris(hydroxy-methyl)methylacrylamide also called THAM] copolymers, acrylic acid/acrylamide copolymers, acrylic acid/N-methylacrylamide copolymers, acrylic acid/N,N-dimethylacrylamide copolymers, acrylic acid/meth-acrylamide copolymers, acrylic acid/N-isopropylacrylamide copolymers, acrylic acid/N-[2-hydroxy-1,1-bis(hydroxymethyl)ethyl]propenamide [or tris(hydroxymethyl)acrylamidomethane or N-tris(hydroxymethyl)methylacrylamide also called THAM] copolymers, copolymers of acrylic acid and of alkyl acrylates of which the carbon chain contains between ten and thirty carbon atoms, and copolymers of AMPS and of alkyl acrylates of which the carbon chain contains between ten and thirty carbon atoms.

The term "branched polymer" denotes a nonlinear polymer which has pendant chains so as to obtain, when this polymer is dissolved in water, a high degree of entanglement resulting in very high viscosities at low shear rate.

The term "crosslinked polymer" denotes a nonlinear polymer in the form of a three-dimensional network which is insoluble in water but which can be swollen in water, so leading to the obtaining of a chemical gel.

When this polyelectrolyte is crosslinked, it is more particularly crosslinked with a diethylene or polyethylene compound in the molar proportion, expressed relative to the monomers used, of from 0.005% to 1%, and preferably from 0.01% to 0.2%, and more particularly from 0.01% to 0.1%. Preferably, the crosslinking agent and/or the branching agent is chosen from ethylene glycol dimethacrylate, diethylene glycol diacrylate, sodium diallyloxyacetate, ethylene glycol diacrylate, diallyl urea, triallylamine, trimethylol propanetriacrylate or methylene bis(acrylamide), and allylsucrose.

When the inverse latex is used during the step of preparing the adjuvant composition prepared in step a) which is the subject of the method of the invention, it generally comprises from 1% to 5% by mass of an emulsifying system of water-in-oil (W/O) type.

The term "emulsifying system of water-in-oil (W/O) type" denotes, in the previous definition, either a single surfactant or a mixture of surfactants on the condition that said mixture has an HLB value that is sufficiently low to induce water-in-oil emulsions. As emulsifier of water-in-oil type, mention is, for example, made of sorbitan esters, for instance sorbitan oleate, such as the product sold by the company SFPPIC under the name Montane™ 80, sorbitan isostearate, such as the product sold by the company SEPTIC under the name Montane™ 70 or sorbitan sesquioleate, such as the product sold by the company SEPPIC under the name Montane™ 83. There are also some polyethoxylated sorbitan esters, for example pentaethoxylated sorbitan monooleate, such as the product sold by the company SEPPIC under the Montanox™ 81, or pentaethoxylated sorbitan isostearate, such as the product sold under the number Montanox™ 71 by the company SEPPIC. There is also diethoxylated oleocetyl alcohol, such as the product sold under the name Simulsol™ OC 72 by the company SEPPIC, polyesters having a molecular weight between 1000 and 3000, produced from condensation between a poly(isobutenyl)succinic acid or the anhydride thereof and diethanolamine, such as Hypermer™ 2296 sold by the company UNIQEMA, or finally, block copolymers having a molecular weight between 2500 and 3500, such as Hypermer™ B246 sold by the company UNIQEMA or Simaline™ IS 200 sold by the company SEPPIC.

When the inverse latex is used during the step of preparing the adjuvant composition prepared in step a) which is the subject of the method of the invention, it generally comprises from 2% to 8% by mass of an emulsifying system of oil-in-water (O/W) type.

The term "emulsifying system of oil-in-water (O/W) type" denotes, in the previous definition, either a single surfactant or a mixture of surfactants on the condition that said mixture has an HLB value sufficiently high to induce oil-in-water emulsions. As emulsifiers of oil-in-water type, mention may, for example, be made of ethoxylated sorbitan esters, such as sorbitan oleate polyethoxylated with 20 mol of ethylene oxide, sold by the company SEPPIC under the name Montanox™ 80, sorbitan laurate polyethoxylated with 20 mol of ethylene oxide, sold by the company SEPPIC under the name Montanox™ 20, castor oil polyethoxylated with 40 mol of ethylene oxide, sold under the name Simulsol™ OL50, decaethoxylated oleodecyl alcohol, sold by the company SEPPIC under the name Simulsol™ OC 710, heptaethoxylated lauryl alcohol, sold under the name Simulsol™ P7 or sorbitan monostearate polyethoxylated with 20 mol of ethylene oxide, sold by the company SEPPIC under the name Montanox™ 60.

A polymer obtained by emulsion polymerization, resulting in the inverse latex forming the basis of the preparation of the adjuvant composition prepared during step a) of the method which is the subject of the invention, advantageously used is chosen from the group made up of totally or partially salified acrylic acid homopolymer, partially or totally salified methacrylic acid homopolymer, acrylic acid/2-methyl-[(1-oxo-2-propenyl)amino]-1-propanesulfonic acid copolymers, acrylamide/2-methyl-[(1-oxo-2-propenyl)amino]-1-propanesulfonic acid copolymers, 2-methyl-[(1-oxo-2-propenyl)amino]-1-propanesulfonic acid/(2-hydroxyethyl) acrylate copolymers, and even more advantageously poly(sodium acrylate).

The proportion by mass of said at least one inverse latex in the adjuvant composition prepared during step a) of the method which is the subject of the invention is between 0.5% and 30% of the total mass of the adjuvant composition, and preferably between 5% and 15% of the total mass of the adjuvant composition.

During step a) of the method which is the subject of the present invention, an immunostimulant substance may be added. The immunostimulant substance is, for example, chosen from one or more conventional immunostimulants, such as Avridine™, N,N-dioctadecyl-N',N'-bis(2-hydroxyethyl) propanediamine, MDP (muramyl dipeptide) derivatives, in particular threonyl-MDP, mycolic acid derivatives or lipid A derivatives. Such a substance is more particularly an ionized substance.

The ionized substance is, for example, chosen from one or more water-soluble metal cation organic salts, such as, for example, calcium gluconate, manganese gluconate, aluminum salicylate or soluble aluminum acetate. When the adjuvant composition according to the invention comprises a pharmaceutically acceptable salt, this salt is at a concentration of from 0.02 to 3000 mg/cm$^3$, preferably 0.1 to 1000 mg/cm$^3$, more preferably from 0.1 to 150 mg/cm$^3$. Insoluble salts generally used as adjuvants of immunity, such as aluminum hydroxide or calcium phosphate, can also be used.

According to one aspect of the invention, during step a), at least one surfactant which is hydrophilic in nature, intended to stabilize the emulsion, is added. The HLB of said at least one surfactant which is hydrophilic in nature is between 10 and 15.

The composition prepared in step a) comprises between 0.1% and 15% of said at least one surfactant, and preferably between 0.1% and 5% of said at least one surfactant.

For the purpose of the present invention, the HLB number of a surfactant is calculated using the formula HLB=20 (1−$I_s/I_a$) in which $I_s$ represents the saponification index and $I_a$ represents the acid index of the fatty acid used for the preparation of said surfactant. In the case of a mixture of surfactants, the HLB of the mixture is the weighted sum of the HLBs of each surfactant. These two indices, saponification and acid indices, are determined by methods described in the European pharmacopeia.

According to another particular aspect of the invention, the composition obtained during step a) of the method which is the subject of the present invention has an oily phase content by mass of between 0.1% and 5% of the total mass of the composition obtained during step a) of the method which is the subject of the present invention, and preferably between 0.2% and 1% by mass.

The surfactants with a hydrophilic nature that are used are generally chosen from modified fatty substances.

The modified fatty substances used in the context of the present invention may be of mineral, plant or animal origin. As modified fatty substances of mineral origin, there are oils of petroleum origin.

As modified fatty substances of plant origin, there are modified plant oils, for example modified groundnut, olive, sesame, soya bean, wheatgerm, grapeseed, sunflower, castor, flax, corn, copra, palm, walnut, hazelnut or rapeseed oils.

As modified fatty substances of animal origin, there are, for example, modified squalane, modified squalene, modified spermaceti oil or modified tallow oil.

The term "modified fatty substances" denotes in particular alkoxylated derivatives of fatty substances, and more particularly alkoxylated derivatives of oils or alkoxylated derivatives of alkyl esters of oils, and more particularly ethoxylated and/or propoxylated derivatives of oils or ethoxylated and/or propoxylated derivatives of methyl, ethyl, linear or branched propyl or linear or branched butyl esters of said oils. A subject of the invention is more specifically a composition as defined above, in which the modified fatty substance is chosen from ethoxylated derivatives of oils having a number of moles of ethylene oxide of between 1 and 10.

The term "modified fatty substances" also denotes fatty acid esters of polyols or fatty alcohol ethers of polyols, and more particularly esters of fatty acids with a hexyl, for instance sorbitol or mannitol, or esters of fatty acids with a hexyl anhydride, such as sorbitan or mannitan, alkoxylated derivatives of fatty acid esters of polyols or alkoxylated derivatives of fatty alcohol ethers of polyols, such as alkoxylated fatty acid triglycerides, alkoxylated fatty acid esters of polyglycerol, and more particularly alkoxylated esters of fatty acids with a hexyl, for instance sorbitol or mannitol, or alkoxylated esters of fatty acids with a hexyl anhydride, such as sorbitan or mannitan, having a number of moles of ethylene oxide of between 1 and 20.

The term "fatty acid esters of polyols" denotes, in the context of the present invention, fatty acid monoesters of polyols or fatty acid polyesters of polyols, for instance fatty acid diesters of polyols or fatty acid triesters of polyols. The same is true for the polyalkoxylated derivatives of said esters.

The term "fatty acid ethers of polyols" denotes, in the context of the present invention, fatty acid monoethers of polyols or fatty acid polyethers of polyols, for instance fatty acid diethers of polyols or fatty acid tri ethers of polyols. The same is true for the polyalkoxylated derivatives of said ethers.

The modified fatty substances may be chosen from ethoxylated derivatives of fatty acid esters of polyols or ethoxylated derivatives of fatty alcohol ethers of polyols, and more particularly ethoxylated esters of fatty acids with a hexyl, for instance sorbitol or mannitol, or ethoxylated esters of fatty acids with a hexyl anhydride, such as sorbitan or mannitan, having a number of moles of ethylene oxide of between 5 and 10.

As fatty acids suitable for the preparation of the modified fatty substances described above, there are those containing, on average, from 12 to 22 carbon atoms, for instance those containing from 16 to 18 carbon atoms, such as oleic acid, ricinoleic acid or isostearic acid, and advantageously fatty acids which are liquid at 20° C.

According to one aspect of the invention, during step b), at least one immunostimulant chosen from saponins, animal and/or plant and/or mineral and/or synthetic oils, surfactants, aluminum hydroxide, lecithins and lecithin derivatives is added.

According to one particular aspect of the invention, the vaccine obtained during step b) comprises between 10% and 20% of the preparation obtained in step a) and between 80% and 90% of an antigenic medium.

A subject of the invention is also a vaccine composition comprising between 10% and 20% of a preparation obtained according to step a) of the method as described above, and between 80% and 90% of an antigenic medium.

The vaccine composition as described above can be used as a preventive or curative medicament. Depending on the nature of the antigen or of the in vivo generator, a composition according to the invention can be administered to fish, shellfish such as shrimp, poultry, in particular geese, turkeys, pigeons and chickens, to canines such as dogs, to felines such as cats, to pigs, to primates, to bovidae, to members of the sheep family, to horses, to rodents such as rats, lagomorphs such as rabbits, caprinae such as goats, and large mammals such as elephants. The composition according to the invention may also be administered to humans.

The composition can be administered conventionally via the parenteral route, in particular by subcutaneous, intramuscular or intraperitoneal injection. It can also be administered orally, nasally, ocularly, by immersion or by balneation.

Finally, a subject of the invention is the use of an adjuvant composition obtained according to step a) of the method as described above, for the preparation of a vaccine composition.

The percentages used throughout the application represent proportions by mass.

Figure 2:
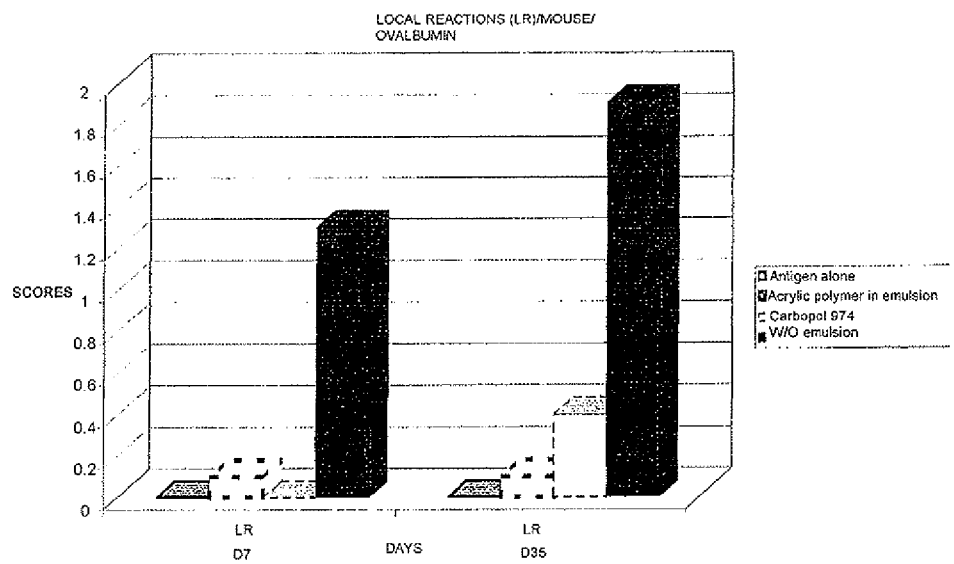

Very surprisingly, comparison of the adjuvant properties of dispersions of inverse latexes relative to polymers having the same chemical composition but obtained by solvent-phase synthesis followed by precipitation, demonstrates much greater adjuvant effects both on the humoral response (FIG. 1) and on the cellular response, accompanied by a high degree of innocuousness (FIG. 2).

The following examples illustrate the invention without, however, limiting it.

EXAMPLE 1

Poly(Sodium Acrylate)-Based Adjuvant Composition Obtained in a Water-in-Mineral Oil Emulsion A fluid mineral oil, "Marcol© 52", supplied by Exxon is used. The polymer emulsion obtained after polymerization is in the form of a viscous, white, oily gel. The composition thereof is 30% of mineral oil (the continuous phase), 5% of surfactant intended to stabilize the emulsion, 25% of poly (sodium acrylate) and 40% of water. On contact with an aqueous antigenic solution buffered at pH 7, at 3%, the polymer-in-oil emulsion inverts so as to give a fluid dispersion of polymer containing traces of oil.

EXAMPLE 2

Poly(Sodium Acrylate)-Based Vaccine Adjuvant Obtained by Emulsion Polymerization A dispersion in water containing 10% of the polymer described in example 1 is prepared with sufficient mechanical stirring. The viscosity can be adjusted by adding inert ionized substances (salts) (for example, sodium chloride) or immunostimulant substances (for example, manganese gluconate). This ready-to-use gel can be redispersed, at the required concentration, in the antigenic medium under consideration. The addition, to the gel, of supplementary surfactants intended to stabilize the oil-in-water dispersion can also be carried out.

EXAMPLE 3

Vaccine Containing Poly(Sodium Acrylate), Obtained by Emulsion Polymerization A vaccine is made up of 85% of antigenic medium to which 15% of the preparation described in example 2 is added. The addition of other immunostimulants, such as, for example, saponins, animal and/or plant and/or mineral and/or synthetic oils, surfactants, aluminum hydroxide, lecithins and lecithin derivatives, is possible.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for preparing a vaccine, said method comprising:
    a step a) of preparing an adjuvant composition by dispersing, in a physiologically acceptable aqueous solution, at least one inverse latex or a powder of polymer resulting from the atomization of said inverse latex;
    wherein the inverse latex comprises at least one branched or crosslinked, anionic polyelectrolyte comprising a totally or partially salified acrylic acid homopolymer and further comprising a step a) (i) of adding one or more water soluble metal cation organic salts
    a step b) of mixing the composition obtained in step a) into an antigenic medium comprising an antigen, to form a composition capable of eliciting an immune response to the antigen upon administration to a subject.

2. The method of claim 1, wherein during step a) at least one additional immunostimulant substance is added.

3. The method of claim 1, wherein step b) comprises mixing 10% to 20% of the preparation obtained in step a) with 80% to 90% of the antigenic medium.

4. The method of claim 1, further comprising, during step b):
    a step of adding at least one immunostimulant chosen from saponins, animal and/or plant and/or mineral and/or synthetic oils, surfactants, aluminum hydroxide, lecithins and lecithin derivatives.

5. The method of claim 2, wherein step b) comprises mixing 10% to 20% of the preparation obtained in step a) with 80% to 90% of the antigenic medium.

6. The method of claim 2, further comprising, during step b):
    a step of adding at least one immunostimulant chosen from saponins, animal and/or plant and/or mineral and/or synthetic oils, surfactants, aluminum hydroxide, lecithins and lecithin derivatives.

7. The method of claim 3, further comprising, during step b):
    a step of adding at least one immunostimulant chosen from saponins, animal and/or plant and/or mineral and/or synthetic oils, surfactants, aluminum hydroxide, lecithins and lecithin derivatives.

8. The method of claim 1, wherein the one or more water-soluble metal cation organic salts comprises manganese gluconate.

9. The method of claim 1, wherein the formed composition is a vaccine.

10. The method of claim 1, wherein the formed composition is a vaccine.

11. The method of claim 8, wherein the formed composition is a vaccine.

* * * * *